(12) United States Patent
Mueller

(10) Patent No.: US 10,137,067 B2
(45) Date of Patent: Nov. 27, 2018

(54) TWO-COMPONENT PRODUCTS IN BAGS FOR THE OXIDATIVE DYEING OF KERATIN FIBRES

(71) Applicant: Henkel AG & Co. KGaA, Duesseldorf (DE)

(72) Inventor: Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/537,453

(22) PCT Filed: Nov. 17, 2015

(86) PCT No.: PCT/EP2015/076763
§ 371 (c)(1),
(2) Date: Jun. 19, 2017

(87) PCT Pub. No.: WO2016/096280
PCT Pub. Date: Jun. 23, 2016

(65) Prior Publication Data
US 2018/0263872 A1    Sep. 20, 2018

(30) Foreign Application Priority Data
Dec. 18, 2014 (DE) .................. 10 2014 226 366

(51) Int. Cl.
| | | |
|---|---|---|
| *A61Q 5/10* | (2006.01) | |
| *A61K 8/22* | (2006.01) | |
| *A61Q 5/08* | (2006.01) | |
| *A61K 8/55* | (2006.01) | |

(52) U.S. Cl.
CPC .............. *A61K 8/22* (2013.01); *A61K 8/55* (2013.01); *A61Q 5/08* (2013.01); *A61Q 5/10* (2013.01); *A61K 2800/43* (2013.01); *A61K 2800/51* (2013.01); *A61K 2800/87* (2013.01); *A61K 2800/882* (2013.01)

(58) Field of Classification Search
CPC ........ A61Q 5/10; A61K 8/22; A61K 2800/87; A61K 2800/51; A61K 2800/43
See application file for complete search history.

(56) References Cited

U.S. PATENT DOCUMENTS

| | | |
|---|---|---|
| 2009/0108021 A1 | 4/2009 | Hansen et al. |
| 2009/0236363 A1 | 9/2009 | Haley et al. |
| 2011/0215113 A1 | 9/2011 | Hansen et al. |
| 2016/0158125 A1 | 6/2016 | Neuba et al. |
| 2016/0158129 A1 | 6/2016 | Neuba et al. |
| 2016/0159552 A1 | 6/2016 | Neuba et al. |

FOREIGN PATENT DOCUMENTS

| | | | |
|---|---|---|---|
| DE | 10 2008 017 104 A1 * | 10/2009 | .......... B65D 83/00 |
| DE | 102008017104 A1 | 10/2009 | |
| EP | 2738117 A1 | 6/2014 | |
| GB | 2195718 A | 4/1988 | |

OTHER PUBLICATIONS

English translation (Aug. 9, 2018) of the Patent No. DE 10 2008 017 104 A1.*
EPO, International Search Report and Written Opinion issued in International Application No. PCT/EP2015/076763, dated Jan. 25, 2016.

* cited by examiner

*Primary Examiner* — Eisa B Elhilo
(74) *Attorney, Agent, or Firm* — Lorenz & Kopf, LLP

(57) ABSTRACT

Products for oxidatively changing the color of keratinic fibers include at least two preparations (A) and (B), which are produced separately from one another. The first preparation (A) includes, in a cosmetic carrier, (A1) hydrogen peroxide and (A2) at least one chelating agent chosen from a group of specific chelating agents. The second preparation (B) includes, in a cosmetic carrier, (B1) at least one alkalizing agent. The preparation (A) is produced in a first container (container A). The first container includes at least two layers: an inner layer that includes a layer of a synthetic polymer (I) and an outer layer that includes a metal layer. Preparation (B) is produced in a second container (container B), which includes at least two layers: an inner layer that includes a layer of a synthetic polymer (I) and an outer layer that includes a metal layer.

19 Claims, No Drawings

TWO-COMPONENT PRODUCTS IN BAGS FOR THE OXIDATIVE DYEING OF KERATIN FIBRES

CROSS-REFERENCE TO RELATED APPLICATION

This application is a U.S. National-Stage entry under 35 U.S.C. § 371 based on International Application No. PCT/EP2015/076763, filed Nov. 17, 2015 which was published under PCT Article 21(2) and which claims priority to German Application No. 102014226366.2, filed Dec. 18, 2014, which are all hereby incorporated in their entirety by reference.

TECHNICAL FIELD

The present disclosure is in the field of cosmetics and relates to products for changing the color of keratinic fibers oxidatively, the products comprising at least two preparations (A) and (B), which are formulated separately from one another. Preparation (A) contains hydrogen peroxide and special complexing agents and preparation (B) contains at least one alkalizing agent. Furthermore, the two preparations (A) and (B) are made up separately from one another in two containers (A) and (B), which preferably are pouches, each comprising at least two layers. The inner layer of each receptacle is a synthetic polymer layer, whereas the outer layer of each receptacle comprises a metal layer, which preferably is an aluminum foil.

BACKGROUND

The change in the color of keratinic fibers, especially of hair, represents an important area of modern cosmetics. In this way, the appearance of the hair can be adapted to current fashion currents as well as to the individual desires of the particular person. Someone of ordinary skill in the art knows various possibilities for changing the color of hair.

The color of hair can be changed temporally by using substantive dyes. In this case, ready-made dyes diffuse from the colorant, which has already been produced, into the hair fiber. The dyeing with substantive dyes is associated with slight hair damage. However, a disadvantage is the low durability and the rapid leaching of the dyeings obtained with substantive dyes.

If the consumer wants a long lasting color result or a shade, which is lighter than his initial hair color, oxidative color changing agents are usually used. So-called oxidation dyes are used for permanent, intensive dyeings with corresponding genuiness properties. Such dyes usually contain oxidation dye precursors, so-called developer components and coupler components, which form the actual dyes under the influence of oxidizing agents—generally hydrogen peroxide. Oxidation dyes are distinguished by outstanding, long-lasting dyeing results.

Oxidative color-changing agents usually are marketed in the form of two-component compositions, in which two different preparations are present separately in two separate containers and have to be mixed with one another shortly before use.

The first preparation is a formulation, which is usually made acidic for reasons of stability and which contains hydrogen peroxide as an oxidizing agent in concentrations of 1 to 12% by weight. The oxidizing agent usually is formulated as an emulsion or dispersion and generally is made available in a plastic bottle with a reclosable outlet opening (developer bottle).

The second preparation is an alkaline formulation, which is often in the form of a cream or a gel and which additionally also contains the precursors of the oxidation dye if, at the same time with the brightening, a color change is also desired. This second component is provided in most cases in a tube, more rarely in a plastic container or in a glass bottle.

To prepare the ready-for-use mixture, the consumer must mix the two preparations with one another shortly before use. For this purpose, the alkaline cream or gel component is usually transferred completely from the tube or the glass or plastic container into the developer bottle, the two components are then mixed together as completely and homogeneously as possible by shaking and finally removed through an outlet opening in the head of the developer bottle.

However, this separate mixing process has a series of disadvantages for the user. Thus, the incomplete emptying of the tube can alter the quantitative ratio of the two components, which leads to deviations in the desired coloring result. If the two components are not shaken or mixed long enough, the application mixture is inhomogeneous with the result that a non-uniform color results. In addition, it is also desirable for reasons of user comfort to dispense with this mixing step completely.

In order to avoid these disadvantages, multi-chamber containers with a common dispenser opening were developed, in which the two components are mixed in the valve or dispenser during the exit. Removal of the application mixture through the dispenser makes mixing of the components by the user superfluous and has increased the application comfort significantly.

In an embodiment, which is particularly convenient for the user, the multi-chamber container with a common dispensing opening is an aerosol product. As a result of the propellant present in the aerosol product, the two preparations can be removed uniformly in the form of a homogeneous foam if the user exerts pressure on the valve or the dispenser. Since the two preparations are mixed in the valve or dispenser during removal, mixing, shaking or stirring by the user, which is associated with effort, is no longer required.

The outer wall of very many aerosol containers includes metal. The two preparations, which are to be mixed at the beginning of the oxidative color changing process, contain very reactive chemicals with strong alkalizing agents and oxidizing agents and have special requirements for storage and packaging in the aerosol system. In order to avoid unwanted side reactions (such as the corrosion of the metal aerosol container), these two preparations are therefore not filled directly into two chambers of an aerosol container, but are initially filled into two separate pouches, which are inside the metal aerosol container.

For removing the two preparations out of the pouches, two tubes, which are connected with the valve, protrude into each pouch. When the valve is actuated, the preparations are then pressed by the propellant gas from each pouch through the two pipes in the direction of the valve, mixed with one another just below or just above the valve, and then emerge from the valve in the form of the application mixture.

The exact construction of these two-chamber aerosol systems, which are provided with pouches, is disclosed, for example, in EP 2009/0108021 A1 or in US patent 2009/0108021 A1, to the contents of which reference is made here.

In order to prevent escape of the contents (particularly of the reactive agents) from the pouches, the latter usually includes at least two layers, an inner polymer layer and an outer metal layer (such as, for example, aluminum). The outer metal or aluminum layer is highly impermeable to gases and prevents the escape of oxygen (caused by the decomposition of hydrogen peroxide), the evaporation of water or ammonia, and also the escape of all other volatile constituents, such as, for example, solvents.

In order to prevent direct contact between the preparations and the metal or aluminum foil, at least one additional polymer layer is applied to the aluminum layers on the inside of the pouches. This inner polymer layer is, for example, a layer of a synthetic polyolefin polymer. These two layers may also be connected to one another by an adhesive layer, which may include an adhesive polymer. In this case, the pouches comprise at least three layers: an inner layer of a synthetic polyolefin polymer, a middle layer of an adhesive polymer and an outer layer of an aluminum foil.

For lining or protecting the outer metal or aluminum layer further, the latter may also be coated with a further polymer layer on the outside. In this case, the pouches comprise at least four layers: an inner layer of a synthetic polyolefin polymer, a middle layer of an adhesive polymer and an outer layer of an aluminum foil and, on the very outside, once more a layer of a synthetic polyolefin polymer.

A general disadvantage of this pouch structure is that the two layers of an inner (polyolefin) polymer and, if appropriate, an intermediate adhesive polymer, cannot completely prevent the penetration of the hydrogen peroxide up to the aluminum foil. If the hydrogen peroxide then undesirably diffuses through both polymer layers, hydrogen peroxide and aluminum can react with one another, which can lead to the decomposition of hydrogen peroxide, to the formation of oxygen and to the inflation of the pouch. Because of these side reactions, the shelf life of the hydrogen peroxide-containing preparations in the aforementioned pouches is greatly reduced.

BRIEF SUMMARY

Products for oxidatively changing the color of keratinic fibers are provided herein. The products include at least two preparations (A) and (B), which are produced separately from one another. The first preparation (A) comprises, in a cosmetic carrier, (A1) hydrogen peroxide and (A2) at least one chelating agent chosen from the group of 1-hydroxyethane-1,1-diphosphonic acid (HEDP), ethylenediaminetetramethylenephosphonic acid (EDTMP), diethylenetriaminepentamethylenphosphonic acid (DTPMP), aminotrimethylenephosphonic acid (ATMP), N,N-bis[2-[bis(carboxymethyl)amino]ethyl]glycine, ethylene-diamine-N,N'-disuccinic acid (EDDS), 2-hydroxypropylenediamine-N,N'-disuccinic acid (HPDDS), ethylenediamine-N,N'-diglutaric acid (EDDG), ethylenediamine-N,N'-bis-(orthohydroxyphenyl)acetic acid (EDDHA). The second preparation (B) includes, in a cosmetic carrier, (B1) at least one alkalizing agent. The preparation (A) is produced in a first container (container A). The first container includes at least two layers. An inner layer of the container A includes a layer of a synthetic polymer (I) and an outer layer of the container A includes a metal layer. Preparation (B) is produced in a second container (container B), which includes at least two layers. An inner layer of the container B includes a layer of a synthetic polymer (I) and an outer layer of the container B includes a metal layer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was therefore the objective of the present disclosure to find a new product for oxidative color changes, which is based on a multichamber aerosol system that is provided with pouches and also enables prolonged storage of a hydrogen peroxide-containing preparation in these pouches.

Surprisingly, it was now discovered that the addition of special complexing or chelating agents to the preparation, which contains hydrogen peroxide, prevents the reaction of the hydrogen peroxide with the metal layer of the pouches in a multichamber aerosol system.

A first object of the present disclosure is a product for oxidatively changing the color of keratinic fibers, comprising at least two preparations (A) and (B), which are produced separately from one another, wherein
the first preparation (A) contains, in a cosmetic carrier,
  (A1) hydrogen peroxide and
  (A2) at least one chelating agent from the group comprising 1-hydroxyethane-1,1-diphos-phonic acid (HEDP), ethylendiaminetetramethylenphosphonic acid, Diethylenetriaminpentamethylenephosphonic acid (DTPMP), aminotrimethylenephos-phonic acid (ATMP), N,N-bis[2-[bis(carboxymethyl)amino]ethyl]glycine, ethylenediamine-N,N'-disuccinic acid (EDDS), 2-hydroxypropylenediamine-N,N'-disuccinic acid (HPDDS), ethylenediamine-N,N'-diglutaric acid (EDDG), ethylenediamine-N,N'-bis-(orthohydroxyphenyl)acetic acid (EDDHA),
the second preparation (B), in a cosmetic carrier, contains
  (B1) at least one alkalizing agent,
preparation (A) is produced in a first container (container A), which comprises at least two layers, wherein
  an inner layer of the container A comprises a layer of a synthetic polymer (I) and
  an outer layer of the container A comprises a metal layer and
preparation (B) is produced in a second container (container B), which comprises at least two layers, wherein
an inner layer of container B comprises a layer of a synthetic polymer (I) and
an outer layer of container B comprises a metal layer.

The preparation (B) is prepared in a second container (container B), which comprises at least two layers, wherein
an inner layer of the container B comprises one layer of a synthetic polymer (I) and
an outer layer of the container B comprises a layer of metal.

Keratinic fibers keratin-containing fibers or keratin fibers are understood to be wool, fur, feathers and especially human hair. Although the compositions as contemplated herein primarily are suitable for lightening and coloring keratin fibers, there is, in principle, nothing against using them also in other fields.

The preparations (A) and (B) in the containers (A) and (B) contain the essential constituents in a cosmetic carrier, preferably in a suitable aqueous, alcoholic or aqueous-alcoholic carrier. For the purpose of oxidative dying, such carriers may, for example, be crèmes, emulsions or also surfactant-containing foaming solutions, such as, for example, shampoos, foam aerosols, foam formulations or other preparations, which are suitable for application on hair. Particular preference is given to the preparations (A) and/or (B) if they are creams or emulsions. The term "oxidative color changing agent" as contemplated herein refers to oxidative dyes, which change the color of the keratin fibers oxidatively, that is, by the use of the hydrogen peroxide contained in preparation (A).

If the inventive product does not contain any further dyes in addition to the hydrogen peroxide, the oxidative color change is exclusively a blonding, bleaching or lightening which is caused by the destruction of the coloring pigments of the keratin, the melanin. In addition, the products for oxidatively changing color as contemplated herein may, however, also contain one or more oxidation dye precursors (of the developer and of the coupler type). In this case, the hydrogen peroxide contained in the product initiates a dye-forming reaction between the developer and the coupler and the oxidative color change in this case is both a more or less brighter coloration as well as a dyeing.

Oxidation dye precursors, additionally contained, are usually prepared together with the alkalizing agent in preparation (B).

The product as contemplated herein comprises at least two preparations (A) and (B), which are prepared separately from one another.

Preparation (A) includes
(A1) hydrogen peroxide and
(A2) at least one chelating agent from the group comprising 1-hydroxyethane-1,1-diphosphonic acid (HEDP), ethylenediaminetetramethylenephosphonic acid (EDTMP), diethylenetriaminepentamethyle-nephosphonic acid (DTPMP), aminotrimethylenephosphonic acid (ATMP), N,N-bis[2-[bis (carboxymethyl) amino] ethyl] glycine, ethylenediamine-N, N'-disuccinic acid), 2-hydroxypropylenediamine-N, N'-disuccinic acid (HPDDS), ethylenediamine-N, N'-diglutaric acid (EDDG), 2-hydroxypropylenediamine-N,N'-disuccinic acid (HPDDS), ethylenediamine-N,N'-bis-(orthohydroxyphenyl) acetic acid (EDDHA), diethylenetriaminepentaacetic acid (DTPA) and/or a physiologically tolerated salt hereof. In preparation (A), hydrogen peroxide (A1) itself or one of its solid addition products with an organic or inorganic compound is used. As contemplated herein, the addition products with urea, melamine, polyvinylpyrrolidinone, sodium carbonate and sodium borate come into consideration as solid addition products.

Preferably, hydrogen peroxide itself is used as an aqueous solution. The concentration of a hydrogen peroxide solution in the material as contemplated herein is determined, on the one hand, by legal requirements and, on the other, by the effect desired; preferably from about 6 to about 12% by weight solutions in water are used. Preparations (A), preferred as contemplated herein, contain hydrogen peroxide (A1) in an amount of from about 0.5 to about 20% by weight, preferably from about 1.5 to about 17.0% by weight, particularly from about 1.5 to about 15% by weight and more particularly of from about 2.5 to about 12.0% of the total weight of the preparation (A).

In a particular preferred embodiment, the product as contemplated herein is exemplified in that the first preparation (A) contains, based on the total weight of the preparation (A)

(A1) hydrogen peroxide in an amount of from about 0.5 to about 20.0% by weight, preferably from about 1.5 to about 17.0% by weight, particularly of from about 1.5 to about 15% by weight and more particularly of from about 2.5 to about 12.0% by weight.

An essential and very central feature of the product as contemplated herein is the addition of at least one chelating agent from group (A2) to the preparation (A), which also contains the hydrogen peroxide (A1).

Chelating agents may also be referred to as complexing agents and are compounds, which are capable of forming chelates. The term chelating agent is a collective term for cyclic compounds, in which metals and groups with lone pairs of electrons are involved in the formation of a ring. This ring formation takes place in this case by formation of coordinate bonds of the central metal ion with one or more multi-tooth ligands, that is, ligands which have more than one free pair of electrons.

That or the chelating agents (A2), contained in preparation (A), are selected from the group comprising
1-hydroxyethane-1,1-diphosphonic acid (HEDP),
ethylenediaminetetramethylenephosphonic acid (EDTMP)
diethylenetriaminepentamethylenephosphonic acid (DTPMP)
aminotrimethylene phosphonic acid (ATMP)
N,N-bis[2-[bis(carboxymethyl)amino]ethyl] glycine,
ethylenediamine-N,N'-disuccinic acid (EDDS)
2-hydroxypropylenediamine-N,N'-disuccinic acid (HPDDS)
ethylenediamine-N,N'-diglutaric acid (EDDG)
ethylenediamine-N,N'-bis-(orthohydroxyphenyl)acetic acid (EDDHA), and/or a physiologically tolerated salts hereof.

1-Hydroxyethane-1,1-diphosphoric acid (HEDP), which is also alternatively referred to as etidronic acid, is a compound of Formula (I) and has the CAS number 2809-21-4.

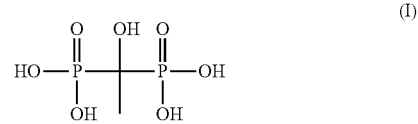
(I)

Suitable physiologically tolerated salts of a HEDP are, for example, the mono-, di-, tri- or the tetrasodium salt, or the mono-, di-, tri- or tetrapotassium salt. Ethylenediaminetetramethylphosphonic acid (EDTMP) is a compound of formula (II) and has the CAS No. 1429-50-1.

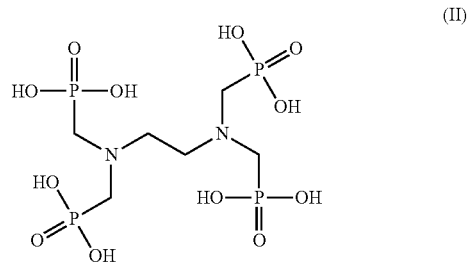 [SMILES: O=P(O)(O)CN(CCN(CP(=O)(O)O)CP(=O)(O)O)CP(=O)(O)O]
(II)

Suitable physiologically tolerated salts of a HEDP are, for example, the mono-, di-, tri-, or the tetrasodium salt, or the mono-, di-, tri- or tetrapotassium salt. Diethylenetriaminepentamethylenephosphonic acid (DTPMP) is a compound of the formula (III) and the substance has the CAS No. 15827-60-8.

(III)

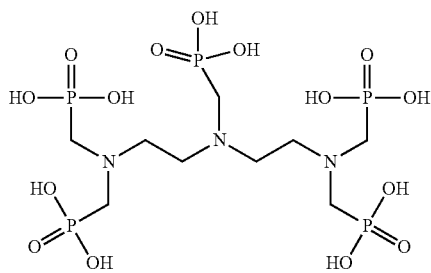

Suitable, physiologically tolerated salts of DTPMP are the mono-, di-, tri-, tetra- and pentasodium salts of this compound and the mono-, di-, tri-, tetra- and pentapotassium salts of this compound. Alternatively, aminotrimethylenephosphonic acid (ATMP) is also referred to as nitrilotris (methylene-phosphonic acid. ATMP has the formula (IV) and the CAS No. 6419-19-8.

(IV)

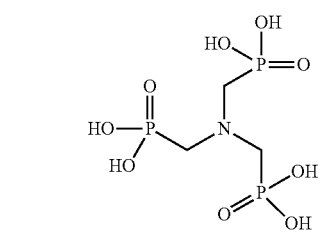

Physiologically tolerated salts hereof are, for example, the mono-, di- or trisodium salt of ATMP or the mono-, di- or tripotassium salt of this compound. N,N-Bis[24bis(carboxymethyl)amino]ethyl]glycine is a compound of Formula (V). Alternative names for this compound are diethylenetriamine pentaacetic acid (DTPA) or also 1,1,4,7,7-diethylenetriaminepentaacetic acid. This compound has the CAS No. 67-43-6

(V)

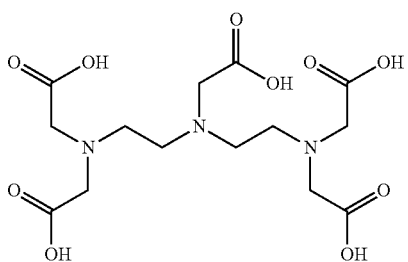

Suitable, physiologically tolerated salts thereof are, for example, the mono-, di-, tri-, tetra or pentasodium salts or the mono-, di-, tri-, tetra or pentapotassium salts of this compound. Ethylenediamine-N,N'-disuccinic acid (EDDS), alternatively also referred to as ethylenediamine disuccinate, is a compound of the Formula (VI). This compound has the CAS No. 20846-91-7

(VI)

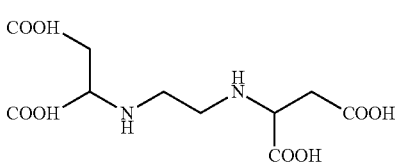

A suitable, physiologically tolerated salt is, for example, the mono-, di-, tri- or tetrasodium salt of the compound or the mono-, di-, tri- or tetrapotassium salt of this compound. The 2-hydroxypropylenediamine-N,N'-disuccinic acid (HPDDS) is a compound of Formula (VII).

(VII)

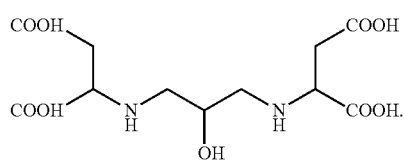

A suitable, physiologically tolerated salt is, for example, the mono-, di-, tri- or tetrasodium salt of the compound or the mono-, di-, tri- or tetrapotassium salt of this compound. Ethylenediamine-N,N'-diglutaric acid (EDDG) is a compound of Formula (VIII).

(VIII)

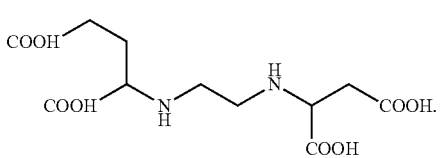

A suitable, physiologically tolerated salt is, for example, the mono-, di-, tri- or tetrasodium salt of the compound or the mono-, di-, tri- or tetrapotassium salt of this compound.

Ethylenediamine-N,N'-bis-(orthohydroxyphenyl) acetic acid (EDDHA) and has the CAS No. 1170-02-1.

(IX)

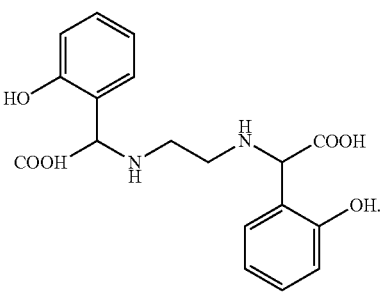

In the course of the work leading to this subject matter as contemplated herein, it has been found that the addition of one or more chelating agents of the Formulas (I) to (IX) to the preparation (A) ensures that the preparation (A), which contains the hydrogen peroxide (A1), can be stored in a multi-layered container or pouch with an outer foil of metal or aluminum, without any unexpected reactions between the hydrogen peroxide and the aluminum foil. In this way, it became possible to store the preparation (A) in a corresponding pouch even for a longer period of several months. The formation of oxygen and the therewith associated inflation of the container or the pouch during the storage period could thus be greatly reduced or even prevented.

To optimize the shelf life, the chelating agent(s) from group (A2) are preferably used in certain amounts in the preparation (A). It was possible to observe the increase in the shelf life already when small amounts of chelating agent (A2) are used. However, the reaction of the hydrogen peroxide with the metal foil of the bag could be prevented effectively particularly when the chelating agent(s) were added to preparation (A) in amounts within a certain range. Thus, the chelating agents (A2) in the preparation (A) are used, particularly in the range from about 0.01 to about 5.5% by weight and preferably from about 0.1 to about 4.5%, more preferably from about 0.3 to about 3.5% by weight and particularly from about 0.7 to about 2.5% by weight, based on the total weight of the preparation (A). The basis for calculating these quantities in % by weight is the total weight of all chelating agents from group (A2), which is related to the total weight of preparation (A).

In a further particularly preferred embodiment, a product as contemplated herein is exemplified in that the first preparation (A) comprises one or more chelating agents (A2) in a total amount of from about 0.01 to about 5.5% by weight, preferably from about 0.1 to about 4.5% by weight, more preferably from about 0.3 to about 3.5% by weight and particularly preferably from about 0.7 to about 2.5% by weight, based on the total weight of preparation (A).

All the chelating agents of Formulas (I) to (IX) have proven to be suitable for increasing the shelf life of preparation (A) in the container (container A) as contemplated herein. However, in this connection, it has turned out that especially the chelating agents, which have at least one phosphorus group, are particularly well-suited. The chelating agents from the following group are therefore particularly effective in increasing the shelf life:
1-hydroxyethane-1,1-diphosphonic acid (HEDP),
ethylenediaminetetramethylenephosphonic acid (EDTMP)
diethylenetriaminepentamethylenephosphonic acid (DTPMP)
aminotrimethylene phosphonic acid (ATMP)
and/or the physiologically tolerated salts hereof.
In a particular preferred embodiment, a product as contemplated herein is exemplified in that the first preparation (A) contains
(A2) at least one chelating agent from the group comprising 1-hydroxyethane-1,1-diphosphonic acid (HEDP), ethylenediaminetetramethylenephosphonic acid (EDTMP), diethylenetriamine-pentamethylenephosphonic acid (DTPMP), aminotrimethylenephosphonic acid (ATMP) and/or a physiologically tolerated salt hereof.
Within this group in turn, the chelating agent 1-hydroxyethane-1,1-diphosphonic acid (HEDP) and the physiologically tolerated salts thereof are most particularly preferred, since it was possible to achieve the best results with this chelating agent.

In a particular preferred embodiment, a product as contemplated herein is exemplified in that the first preparation (A) contains
(A2) 1-hydroxyethane-1,1-diphosphonic acid (HEDP) and/or a physiologically tolerated salts hereof as chelating agents.

Furthermore, a product is also particularly preferred, which is exemplified in that, based on the total weight of the preparation (A), the first preparation (A) contains
(A2) 1-hydroxyethane-1,1-diphosphonic acid (HEDP) and/or the physiologically tolerated salts thereof in a total amount of from about 0.1 to about 5.5% by weight, preferably from about 0.1 to about 4.5% by weight, particularly of from about 0.3 to about 3.5% by weight and more particularly from about 0.7 to about 2.5% by weight.

The chelating agents of group (A2) are compounds of Formulas (I) to (IX) and/or the physiologically tolerated salts hereof. In this connection, physiologically tolerated means suitable for use in cosmetic materials (that is, for application on human hair and human skin). Particularly suitable physiologically tolerated salts are the sodium salts, the potassium salts and/or the ammonium salts ($NH_4$) of the chelating agents of Formulas (I) to (IX).

The amount of hydrogen peroxide used in preparation (A) is determined by the desired brightening effect on the keratinic fibers. If only a slight brightening or primarily a coloration of the keratinic fibers is desired, a hydrogen peroxide content of from about 1.0 to about 2.5% by weight, based on the total weight of the preparation (A), may be sufficient. If, however, the keratinic fibers are to be brightened or bleached more strongly, a higher content of hydrogen peroxide of, for example, up to about 17.0% by weight (based on the total weight of preparation (A)) is selected.

In this connection, it has turned out that the reactions between hydrogen peroxide and the outer metal or aluminum foil of the bag increases as the concentration of hydrogen peroxide increases. Therefore, in order to avoid these reactions, a higher amount of chelating agents from group (A2) should also be selected when higher amounts of hydrogen peroxide (A1) are used.

In other words, with regard to the shelf life of preparation (A) in the container (A), there is a relationship between the amount of hydrogen peroxide (A1) contained in the preparation (A) and the total amount of the chelating agents of group (A2) contained in preparation (A). For this reason, the weight ratio (A1)/(A2) should be set to the optimum value for the most complete suppression of all reactions between hydrogen peroxide and the outer metal layer of the container or the pouch.

It has proven to be particularly advantageous if the weight ratio of the total amount of the hydrogen peroxide (A1) contained in the preparation (A) to the total amount of the chelating agents from group (A2), contained in the preparation (A), that is, the weight ratio of (A1)/(A2) ranges from about 1.0 to about 30.0, preferably from about 2.0 to about 20.0, more preferably from about 3.0 to about 15.0, and more preferably from about 3.3 to about 13.5.

The basis for calculating all data in % by weight here is
  the amount of hydrogen peroxide (A1) contained in preparation (A) in relation to the total weight of preparation (A), and
  the total quantity of all chelating agents of (A2) in preparation (A) in relation to the total weight of preparation (A).
The weight ratio (A1)/(A2) is then determined by dividing these two amounts.

In a further particularly preferred embodiment, a product as contemplated herein is exemplified in that the ratio by weight of the total amount of the hydrogen peroxide (A1), contained in the preparation (A), to the total amount of the chelating agent from group (A2), contained in the preparation (A), that is, the weight ratio (A1)/(A2), ranges from about 1.0 to about 30.0, preferably from about 2.0 to about 20.0, more preferably from about 3.0 to about 15.0, and particularly from about 3.3 to about 13.5.

By the addition of further stabilizers (A3), the side reactions of hydrogen peroxide with the outer metallic layer of the container as contemplated herein can be suppressed even further. Especially the addition of 2,6-dipicolinic acid, benzoic acid and/or salicylic acid has proven to be particularly advantageous in this connection. A particularly good inhibition of side reactions could be observed particularly when (A3), 2,6-dipicolinic acid, benzoic acid, salicylic acid and/or the physiologically tolerated salts of these compounds were contained in a total amount of from about 0.05 to about 4.5% by weight, preferably from about 0.1 to about 1.0% by weight, more preferably from about 0.2 to about 0.9% by weight and particularly from about 0.25 to about 0.7% by weight, in preparation (A). Once again the basis for calculating the quantitative data is the total weight of the aforementioned compounds (A3) as a percentage of the total weight of preparation (A).

In a further particular preferred embodiment, a product as contemplated herein is exemplified in that the first preparation (A), based on the total weight of the preparation (A), additionally contains (A3) 2,6-dipicolinic acid, benzoic acid, salicylic acid and/or their physiologically tolerated salts in an amount of from about 0.05 to about 1.5% by weight, preferably from about 0.1 to about 1.0% by weight, more preferably of from about 0.2 to about 0.9% by weight and more preferably of from about 0.25 to about 0.7% by weight.

The physiologically tolerated salts of 2,6-dipicolinic acid, benzoic acid and salicylic acid are, in particular, the sodium, potassium and ammonium salts of the three compounds.

The second preparation (B) contains at least one alkalizing agent (B1) in a cosmetic carrier.

Preferably, the alkalizing agent(s) (B1) may be selected from the group comprising ammonia, alkanolamines, basic amino acids, as well as inorganic alkalizing agents such as alkali or alkaline earth metal hydroxides, alkali or alkaline earth metal metasilicates, alkali or alkaline earth metal phosphates and alkali or alkaline earth metal hydrogen phosphates. Sodium hydroxide, potassium hydroxide, sodium silicate and sodium metasilicate are preferred inorganic alkalizing agents. Organic alkalizing agents, which can be used as contemplated herein, preferably are selected from monoethanolamine, 2-amino-2-methylpropanol and triethanolamine. The basic amino acids, which can be used as alkalizing agents as contemplated herein, preferably are selected from the group comprising arginine, lysine, ornithine and histidine, arginine being particularly preferred. However, it has been found within the scope of the investigations of the present disclosure, that agents, furthermore preferred as contemplated herein, are exemplified in that they additionally contain an inorganic alkalizing agent. An embodiment of the object as contemplated herein is exemplified in that the second preparation (B) contains at least one alkalizing agent (B1), which is selected from the group comprising ammonia, alkanolamines and basic amino acids, particularly ammonia, monoethanolamine and arginine and/or physiologically tolerated salts thereof.

In order to achieve optimum color change results, preparations (A) and (.(B) preferably are adjusted to a particular pH.

Preparation (A), which contains the hydrogen peroxide, preferably is made acidic for stability reasons and preferably has a pH ranging from about 1.5 to about 5.0, especially from about 2.0 to about 4.5, particularly from about 2.2 to about 4.0 and more particularly from about 2.6 to about 3.5. On the other hand, preparation (B), which contains the alkalizing agent (B1), preferably is made alkaline and preferably has a pH ranging from about 7.5 to about 12.5 especially from about 8.5 to about 11.5 and particularly from about 8.9 to about 10.5.

The ready-to-use agent for the changing the color, which is prepared shortly before use by mixing preparations (A) and (B), preferably is also adjusted to an alkaline pH, since the alkaline pH ensures sufficient swelling of the keratin fibers. The dyeing processes on keratin fibers also usually take place in an alkaline medium. However, in order to preserve the keratin fibers as well as the skin as much as possible, an excessively high pH is not desirable. Preferably therefore, the pH of the ready-two-use material ranges from about 8.0 to about 10.5, especially from about 8.7 to about 10.3, particularly from about 9.0 to about 10.2 and especially from about 9.2 to about 10.1. The pH values given were measured at a temperature of 22° C. with a glass electrode.

In a particularly preferred embodiment, a product as contemplated herein is exemplified in that the first preparation (A) is an aqueous preparation with a pH of from about 1.5 to about 5.0, preferably of from about 2.0 to about 4.5, especially of from about 2.2 to about 4.0 and particularly of from about 2.6 to about 3.5 and the second preparation (B) is an aqueous preparation with a pH of from about 7.5 to about 12.5, preferably of from about 8.5 to about 11.5 and particularly of from about 8.9 to about 10.5.

In preparation (B) is adjusted to the preferred alkaline pH advantageously by the addition of appropriate amounts of the alkalizing agent (B1) as contemplated herein.

Even when preparation (A) preferably is acidic, the addition of small amounts of alkalizing agent may be necessary in order to adjust the pH precisely. Alkalizing agents, which can be used as contemplated herein, may be selected from the group comprising ammonia, alkanolamines, basic amino acids, as well as inorganic alkalizing agents such as alkali or alkaline earth metal hydroxides, alkali or alkaline earth metal metasilicates, alkali or alkaline earth metal phosphates and alkali or alkaline earth metal hydrogen phosphates. Sodium hydroxide, potassium hydroxide, sodium silicate and sodium metasilicates are preferred inorganic alkalizing agents. Organic alkalizing agents which can be used as contemplated herein, preferably are selected from monoethanolamine, 2-amino-2-methylpropanol and triethanolamine. The basic amino acids, which can be used as alkalizing agents as contemplated herein, preferably are selected from the group comprising arginine, lysine, ornithine and histidine, arginine being particularly preferred.

In order to adjust the pH to the low value, preferred as contemplated herein, appropriate amounts of chelating agents from the group (A2) previously described can be used in their respective acidic form in preparation (A). In addition, one or more further acids can be used in the preparations (A) and/or (B) for the fine adjustment of the desired pH. Suitable acids here are, for example, inorganic acids such as hydrochloric acid, sulfuric acid and/or phosphoric acid. However, organic acids such as acetic acid, lactic acid, citric acid, tartaric acid or malic acid may also be used. In this connection, preference is given to the practically odorless organic acids such as lactic acid, citric acid, tartaric acid and/or malic acid.

If the product as contemplated herein is to be used strictly as a brightener, preparation (B) does not contain any further dyes. However, the product as contemplated herein may also be an oxidative dye. In this case, further oxidation dye precursors of the developer and/or coupler type will be added to preparation (B).

Preferred, further developer components with selected from p-phenylenediamine, p-toluylenediamine, 2-(2-hydroxyethyl)-p-phenylenediamine, 2-(1,2-dihydroxyethyl)-p-phenylene-diamine, N,N-bis-(2-hydroxyethyl)-p-phenylenediamine, 2-methoxymethyl-p-phenylenediamine, N-(4-amino-3-methyl-phenyl)-N-[3-(1H-imidazole-1-yl)propyl]amine, N,N'-Bis-(2-hydroxyethyl)-N,N'-bis-(4-aminophenyl)-1,3-diamino-2-propanol, bis-(2-hydroxy-5-aminophenyl)methane, 1,3-Bis-(2,5-diaminophenoxy)-2-propanol, N,N'-bis-(4-aminophenyl)-1,4-diazacycloheptane, 1,1,0-Bis-(2,5-diaminphenyl)-1,4,7,1-0-tetraoxadecane, 4-aminophenol, 4-amino-3-methylphenol, 4-amino-2-aminomethylphenol, 4-amino-2(1,2-dihydroxyethyl)phenol and 4-amino-2-(diethylaminomethyl)phenol, 4,5-diamino-1-(2-hydroxy-ethyl)pyrazole, 2,4,5,6-tetraaminopyrimidine, 4-hydroxy-2,5,6-triaminopyrimidine, 2-Hydroxy-4,5,6-triaminopyrimidin, as well as the physiologically tolerated salts of these compounds. Especially preferred additional developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazole-1-yl)propyl]amine and/or 4,5-diamino-1-(2-hydroxyethyl)-pyrazole as well as the physiologically tolerated salts thereof.

The developers from the group comprising p-phenylenediamine, p-toluenediamine, 2-(2-hydroxyethyl)-p-phenylenediamine, N,N-bis-(2-hydroxyethyl)-p-toluenediamine,2-(2-hydroxyethyl)2-methoxy-methyl-p-phenylendiamine, N-(4-amino-3-methylphenyl)-N-[3-(1H-imidazole-1-yl)propyl]amine, bis-(2-hydroxy-5-aminophenyl)methane, 4-aminophenol, 4-amino-3-methylphenol, provide particular colorations.

For this reason, the use of these developers and/or their physiologically tolerated salts is particularly preferred.

In a further embodiment, the product as contemplated herein is exemplified owing to the fact that the second preparation (B) contains at least one or more oxidation dye precursors from the group comprising p-phenylenediamine, p-toluylenediamine, 2-(2-hydroxy-ethyl)-p-phenylendiamine, N,N-bis-(2-hydroxyethyl)-p-phenylendiamine, 2-methoxymethyl-p-phenylenediamine, N-(4-amino-3-methylphenyl)-N-[3-(1H-imidazole-1-yl)propyl]amine, bis-(2-hydroxy-5-aminophenyl)methane, 4-aminophenol, 4-amino-3-methylphenol, 4,5-diamino-1-(2-hydroxyethyl)-pyrazole, 2,4,5,6-tetraaminopyrimidine, 4-hydroxy-2,5,6-triaminopyrimidine, 2-hydroxy-4,5,6-triamino-pyrimidine and/or the physiologically tolerated salts thereof.

Within the context of oxidative dyeing, coupler components alone do not produce significant dyeing and always require the presence of developer components. Coupler components permit at least one substitution of a chemical group of the coupler by the oxidized form of the developer component. In so doing, they form covalent bonds between the coupler component and the developer component.

As coupler component suitable as contemplated herein, preferably at least one compound of the following class is selected:
  m-aminophenol and/or the derivatives thereof
  m-diaminobenzene and/or the derivatives thereof,
  o-diaminobenzene and/or the derivatives thereof
  o-aminophenol derivatives, such as o-aminophenol,
  naphthalene derivatives with at least one hydroxy group,
  di- or trihydroxybenzene and/or the derivatives thereof
  pyridine derivatives,
  pyrimidine derivatives,
  monohydroxyindole and/or monoaminoindole derivatives,
  monohydroxyindole derivatives and/or monoaminoindole derivatives,
  pyrazolone derivatives, such as 1-phenyl-3-methyl-5-pyrazolone,
  morpholine derivatives such as 6-hydroxybenzomorpholine or 6-aminobenzomorpholine
  quinoxaline derivatives, such as 6-methyl-1,2,3,4-tetrahydroquinoxaline, Mixtures of two or more compounds of one or more of these classes are also contemplated herein within the scope of this embodiment. Preferred are the couplers, which are selected from 3-aminophenol, 5-amino-2-methylphenol, 3-amino-2-chloro-6-methylphenol, amino-2-chloro-6-methylphenol, 2-hydroxy-4-aminohenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diamino-phenoxy)ethanol, 1,3-bis (2,4-diaminophenoxy)propane, 1-methoxy-2-amino-4-(2-hydroxyethyl-amino)benzene, 1,3-Bis(2,4-di-aminophenyl)propane, 2,6-bis(2'-hydroxyethylamino)-1-methylbenzene, 2-({3-[(2-hydroxyethyl)amino]-4-methoxy-5-methylphenylamino)ethanol, 2-({3-[(2-hydroxyethyl)amino]-2-methoxy-5-methyl-phenyl}amino)ethanol, 2-({3-[(2-hydroxyethyl)amino]-4,5-dimethylphenyl}amino)-ethanol, 2[3-morpholine-4-ylphenyl)amino]ethanol, 3-amino-4-(2-methoxyethoxy)-5-methylphenylamine, 1-amino-3-bis-(2-hydroxyethyl)aminobenzene, resorcinol, 2-4-chloro-resorcinol, 1,2,4-trihydroxybenzene, 2-amino-3-hydroxypyridine, 3-amino-2-methylamino-6-methoxypyridine, 2,6-dihydroxy-3,4-dimethylpyridine, 3, 5-diamino-2,6-dimethoxypyridine, 1-phenyl-3-methyl-5-pyrazolone, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and/or 7-hydroxyindoline and physiologically tolerated salts thereof.

In a further embodiment, a product as contemplated herein is exemplified in that the second preparation (B) additionally contains one or more oxidation dye precursors from the group comprising 3-aminophenol, 5-amino-2-methylphenol, 3-amino-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylene diamine, 2-(2,4-diaminophenoxy)ethanol, 1,3-bis(2,4-diaminophenoxy) propane, 1-methoxy-2-amino-4-(2-hydroxyethylamino)benzene, 1,3-bis(2,4-diaminophenyl)propane, 2,6-bis (2'-hydroxyethylamino)-1-methylbenzene, 2-({3-[(2-hydroxyethylamino)-4-methoxy-5-methylphenylamino)ethanol, 2-({3-[(2-hydroxyethylamino]-2-methoxy-5-methylphenyl}ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxy-ethoxy)-5-methylphenylamine, 1-amino-3-bis-(2-hydroxyethyl)aminobenzene, resorcinol,2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridin, 1-phenyl-3-methylpyrazole-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline and/or the physiological tolerated salts thereof.

The preparation (B) may contain the developer and/or the coupler in amounts of from about 0.001 to about 10.0% by weight, based on the total weight of preparation (B). The amounts used depend especially on the shade, to which the keratinic fibers are to be dyed.

For further nuancing, preparation (B) may also contain one or more substantive dyes from the group comprising nonionic, anionic and/or cationic dyes.

Preferred anionic substantive dyes are the compounds known under the international or commercial names of bromophenol blue, tetrabromophenol blue, acid yellow 1, yellow 10, acid yellow 23, acid yellow 36, acid orange 7, acid red 33, acid red 52, pigment red 57:1, acid blue 7, acid green 50, acid violet 43, acid black 1 and acid black 52.

Preferred cationic substantive dyes are basic blue 7, basic blue 26, basic violet 2 and basic violet 14, basic yellow 57, basic red 76, basic blue 16, basic blue 347 (cationic blue 347/dystar), basic blue 99, basic brown 16 and basic brown 17 as well as yellow 87, basic orange 31 and basic red 51.

Nonionic nitro and quinone dyes and neutral azo dyes are particularly suitable as nonionic substantive dyes. Preferred nonionic substantive dyes are those compounds known under the international or commercial names of HC yellow 2, HC yellow 4, HC yellow 5, HC yellow 6, HC yellow 12, HC orange 1, disperse orange 3, HC red 1, HC red 3, HC red 10, HC red 11, HC red 13, HC red BN, HC blue 2, HC blue 11, HC blue 12, disperse blue 3, HC violet 1, disperse violet 1, disperse violet 4, disperse black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxy-ethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydro-quinoxaline, 2-hydroxy-1,4-naphtho-quinone, picramic acid and the salts thereof, 2-amino-6-chloro-4-nitrophenol, 4-ethylamino-3-nitro-benzoic acid and 2-chloro-6-ethylamino-4-nitrophenol. 1-amino-4-(2-hydroxyethyl)-amino-5-chloro-2-nitrobenzene, 4-amino-3-nitrophenol, 1-(2'-ureido-ethyl)-amino-4-nitrobenzene, 2-[(4-amino-2-nitrophenyl)aminobenzoic acid, 6-nitro-1,2,3,4-tetrahydro-quinoxaline, 2-hydroxy-1,4-naphtho-quinone, picramic acid and the salts thereof, 2-amino-6-chloro-4-nitrophenol, 4-ethylamino-3-nitro-benzoic acid and 2-chloro-6-ethylamino-4-nitrophenol.

Preparations (A) and (B) may also contain additional active ingredients, auxiliaries and additives to improve the brightening and/or color performance and to adjust further desired properties of the compositions. For example, one or more of the agents may additionally contain nonionic surfactants, anionic surfactants, cationic surfactants, amphoteric and/or zwitterionic surfactants, nonionic polymers, such as, for example vinylpyrrolidinone/vinyl acrylate copolymers, polyvinylpyrrolidinone, vinylpyrrolidinone vinyl acetate copolymers, polyethylene glycols and polysiloxanes; additional silicones such as volatile or nonvolatile, linear, branched or cyclic, cross-linked or not cross-linked polyalkylsiloxanes (such as dimethicones or cyclomethicones), polyarylsiloxanes and/or polyalkylarylsiloxanes, especially polysiloxane with organofunctional groups, such as substituted or unsubstituted amines (amodimethicones), carboxyl-, alkoxy- and/or hydroxyl groups (dimethicone copolyols), linear polysiloxane (A) polyoxyalkylene (B) block copolymers, grafted silicone polymers; cationic polymers such as quaternized cellulose ethers, polysiloxanes with quaternary groups, dimethyldiallylammonium chloride polymers, acrylamide dimethyldiallylammonium chloride copolymers, dimethylamino ethyl methacrylate vinylpyrrolide ionic copolymers quaternized with diethyl sulfate, vinylpyrrolidinone imidazolinium methochloride copolymers and quaternized polyvinyl alcohol; zwitterionic and amphoteric polymers; anionic polymers such as polyacrylic acids or cross-linked polyacrylic acids; structurants such as glucose, maleic acid and lactic acid, hair conditioning compounds such as phospholipids, such as lecithin and cephalins; perfume oils, dimethyl isosorbide and cyclodextrins; active fiber structure improving ingredients, especially mono-, di- and oligosaccharides such as glucose, galactose, fructose and lactose; dyes for dyeing the material; anti-dandruff materials such as piroctone olamines, zinc omadines and climbazole; amino acids and oligopeptides; protein hydrolysates on an animal and/or vegetable basis, as well as in the form of the fatty acid condensation products thereof or optionally anionically or cationically modified derivatives; vegetable oils; light stabilizers and blockers; active ingredients such as panthenol, pantothenic acid, pantolactone, allantoin, carboxylic acids and the salts thereof as well as bisabolol; polyphenols, especially hydroxycinnamic acids, 6,7-dihydroxycumarins, hydroxybenzoic acids, catechins, tannins, leukoanthocyanidins, anthocyanidins, flavanones, flavones and flavanols; ceramids or pseudoceramids; vitamins, provitamins and vitamin precursors; plant extracts; fats and waxes such as fatty alcohols, beeswax, montan wax and paraffins; swelling materials and penetrants such as glycerin, propylene glycol monoethyl ether, carbonates, hydrogen carbonates, guanidines, ureas as well as primary, secondary and tertiary phosphates; opacifiers such as latex, styrene, PVP und styrene/acrylamide copolymers; pearl shine concentrates such as ethylene glycol monostearate and distearate as well as PEG-3 distearate; pigments and blowing agents such as propellants such as propane/mixtures, $N_2O$, dimethyl ether, $CO_2$ and air.

Reference is made explicitly in this context to the known monographs, for example, Kh. Schrader, Grundlagen und Rezepturen der Kosmetika (Fundamentals and Formulations of Cosmetics), $2^{nd}$ edition, Huthig Buch Verlag, Heidelberg, 1988, which reproduce the corresponding knowledge of someone of ordinary skill in the art.

In the product as contemplated herein, the first preparation (A) is in a first container. An exemplifying feature of this container (A) is that it has at least at least two layers, wherein an inner layer of the container A comprises a layer of a synthetic polymer (I) and an outer layer of the container A comprises a metal layer.

Furthermore, an exemplifying feature of container (B) is that it comprises at least at least two layers, wherein an inner layer of the container B comprises a layer of a synthetic polymer (I) and an outer layer of the container B comprises a metal layer.

The concepts of "inner layer" and "outer layer" define the relative positions here of these two layers to one another. When looking at the containers (A) and (B) filled with contents, the "inner layer" is always closer to the contents of the container than the "outer layer". The "inner layer" of synthetic polymer (I) is always closer to the contents of the pouch than is the "outer layer" of metal.

The containers (A) and B) as contemplated herein comprise at least two layers, namely the "inner layer" of a synthetic polymer (I) and the "outer layer" of a metal. In this case, the names of the "inner layer" and the "outer layer" represent relative terms, not absolute terms. This means that the "inner layer" is necessarily the "innermost layer" only if the containers (A) and (B) comprise exactly two layers. Analogously, the "outer layer" is necessarily the "innermost layer" only if the containers (A) and (B) comprise exactly two layers.

If the containers (A) and (B) comprise one or more further layers, these further layers may be located within the "inner layer", between the "inner layer" and the "outer layer" and/or outside of the "outer layer".

For reasons of costs, it is preferred if the containers (A) and (B) includes the same material and, accordingly, the two inner layers and the two outer layers of the containers (A) and (B) preferably are always the same.

The two containers (A) and (B) preferably are pouches. Accordingly, two identical pouches are preferably used as containers (A) and (B). The total layer thickness of the pouches here preferably is from about 2 to about 400 µm (micrometers), especially from about 10 to about 250 µm (micrometers) and particularly from about 50 to about 200 µm.

In a particularly preferred embodiment, a product as contemplated herein is exemplified in that
the first container (container A) is a pouch with a total layer thickness of from about 2 to about 400 µm (micrometers), preferably of from about 10 to about 250 µm (micrometers) and particularly of from about 50 to about 200 µm (micrometers) and/or
the second container (container B) is a pouch with a total layer thickness of from about 2 to about 400 µm (micrometers), preferably of from about 10 to about 250 µm (micrometers) and particularly of from about 50 to about 200 µm (micrometers).

The total layer thickness is understood to be the sum of the thicknesses of all individual layers present in the pouch.

In a further particularly preferred embodiment, a product as contemplated herein is exemplified in that
the first container (container A) is a pouch with a total layer thickness of from about 50 to about 200 µm (micrometers) and
the second container (container B) is a pouch with a total layer thickness of from about 50 to about 200 µm (micrometers).

The inner layer of the containers (A) and (B), which respectively comprises a layer of a synthetic polymer (I), preferably is a layer of a polyolefin polymer, such as, for example, a "low density" polyethylene (LDPE), a "medium density" polyethylene (MPDE), a high density polyethylene (HDPE), a linear low density polyethylene (LLDPE), a linear "very low density" polyethylene (LVLDPE), an isotactic or syndiotactic polypropylene (PP), an ethylene-propylene copolymer, a 1-polybutene polymer, an ethylene/1-butene copolymer, a propylene/1-butene copolymer, or an ethylene/propylene/1-butene copolymer.

Within this group, the linear "low density" polyethylene (LLDPE) is particularly preferred. The density of the linear "low density" polyethylene preferably is between about 0.91 to about 0.94 g/cc.

In a further particularly preferred embodiment, a product as contemplated herein is exemplified in that
the inner layer of the container A comprises a layer of a synthetic polymer (I) from the group of polyolefins, preferably from polyethylene, polypropylene, a polyethylene/polypropylene copolymer, poly-1-butene, a polyethylene/poly-1-butene copolymer, a poly-propylene/poly-1-butene copolymer/and/or a polyethylene/poly-propylene/poly-1-butene copolymer, and/or the inner layer of the container B comprises a layer of a synthetic polymer (I) from the group of polyolefins, preferably from polyethylene, polypropylene, a polyethylene/polypropylene copolymer, poly-1-butene, a polyethylene/poly-1-butene copolymer, a polypropylene/poly-1-butene copolymer/and/or a polyethylene/poly-propylene/poly-1-butene copolymer.

In a further particularly preferred embodiment, a product as contemplated herein is exemplified in that
the inner layer of the container A comprises a layer of a synthetic polymer (I) of polyethylene (PE) and
the inner layer of the container B comprises a layer of a synthetic polymer (I) of polyethylene (PE).

For the containers (A) and (B), the inner layer of the containers of synthetic polymer (I) preferably has a thickness of from about 20 to about 200 µm (micrometers), preferably of from about 40 to about 150 µm (micrometers) and particularly of from about 50 to about 80 µm (micrometers).

In a further particularly preferred embodiment, a product as contemplated herein is exemplified in that
the inner layer of the container A comprises a layer of a synthetic polymer (I) with a thickness of from about 20 to about 200 µm (micrometers), preferably of from about 40 to about 150 µm (micrometers) and particularly of from about 50 to about 80 µm (micrometers) and/or
the inner layer of the container B comprises a layer of a synthetic polymer (1) having a thickness of from about 20 to about 200 µm (micrometers), preferably of from about 40 to about 150 µm (micrometers) and particularly of from about 50 to about 80 µm (micrometers).

The outer layer of the containers (A) and (B) each comprise a layer of metal, which preferably is aluminum, for example an aluminum foil. The total layer thickness of the aluminum foil preferably is from about 5 to about 50 µm (micrometers), especially from about 7 to about 25 µm (micrometers) and particularly from about 7 to about 12 µm (micrometers).

In a further particularly preferred embodiment, a product as contemplated herein is exemplified in that
the outer layer of container A comprises a layer of aluminum with a thickness of from about 5 to about 50 µm (micrometers), preferably of from about 7 to about 25 µm (micrometers) and particularly of from about 7 to about 12 µm (micrometers) and/or
the outer layer of container B comprises a layer of aluminum with a thickness of from about 5 to about 50 µm (micrometers), preferably of from about 7 to about 25 µm (micrometers) and particularly of from about 7 to about 12 µm (micrometers).

In other words, in a further particularly preferred embodiment, a product as contemplated herein is exemplified in that
the outer layer of container A comprises a layer of aluminum with a thickness of from about 5 to about 50 µm (micrometers), preferably of from about 7 to about 25 µm (micrometers) and particularly of from about 7 to about 12 µm (micrometers), and/or
the outer layer of container B comprises a layer of aluminum with a thickness of from about 5 to about 50 µm (micrometers), preferably of from about 7 to about 25 µm (micrometers) and particularly of from about 7 to about 12 µm (micrometers).

In a further particularly preferred embodiment, a product as contemplated herein is exemplified in that
the outer layer of container A comprises a layer of aluminum with a thickness of from about 5 to about 50

(micrometers), preferably of from about 7 to about 25 μm (micrometers) and especially of from about 7 to about 12 μm (micrometers.

the outer layer of container B comprises an aluminum layer with a thickness of from about 5 to about 50 μm (micrometers), preferably of from about 7 to about 25 μm (micrometers) and particularly of from about 7 to about 12 μm (micrometers).

In other words, in a further particularly preferred embodiment, a product as contemplated herein is exemplified in that
the outer layer of container A comprises aluminum with a thickness of from about 5 to about 50 μm (micrometers), preferably of from about 7 to about 25 μm (micrometers) and particularly of from about 7 to about 12 μm (micrometers), and/or
the outer layer of container B comprises a layer of aluminum with a thickness of from about 5 to about 50 μm (micrometers), preferably of from about 7 to about 25 μm (micrometers) and particularly of from about 7 to about 12 μm (micrometers).

In a further particularly preferred embodiment, a product as contemplated herein is exemplified in that
the outer layer of container A comprises a layer of aluminum with a thickness of from about 5 to about 50 μm (micrometers), preferably of from about 7 to about 25 μm (micrometers) and particularly of from about 7 to about 12 μm (micrometers) and
the outer layer of container B comprises a layer of aluminum with a thickness of from about 5 to about 50 μm (micrometers), preferably of from about 7 to about 25 μm (micrometers) and particularly of from about 7 to about 12 μm (micrometers.

The two containers (A) and (B) may also additionally comprise one or more layers of at least one further polymer (II), which is structurally different from the synthetic polymer (I).

In a further particularly preferred embodiment, a product as contemplated herein is exemplified in that
the containers (A) and (B) comprise a third layer of a synthetic polymer (II), which is structurally different from the synthetic polymer (I).

This third layer made, for example, by a layer of a sticky or adhesive polymer, which is localized between the inner layer of synthetic polymer (I) (preferably polyethylene) and an outer metallic layer (preferably aluminum). Beginning with the interior of the containers (A) or (B), the sequence of layers then always is the internal layer of synthetic polymer (I) (preferably polyethylene), the middle layer of synthetic polymer (2) (adhesive polymer) and the outer layer of metal (preferably aluminum foil).

For example, a polyurethane copolymer, which can be produced by the reaction of an isocyanate with a polyol, is a suitable adhesive polymer (that is, a synthetic polymer (II)). Preferably, this polyurethane copolymer is cross-linked or highly interconnected, for example, 1,6-hexamethylene diisocyanate, 2,2,4-trimethyl-hexamethylene diisocyanate and the lysine ester diisocyanate, aliphatic polyisocyanates with hydrogenated diphenylmethane diisocyanate, isophorone diisocyanate or hydrogenated tolylene diisocyanate, or aromatic polyisocyanates such as, for example, tolylene diisocyanate, 4,4'-diphenylmethane diisocyanate, naphthylene diisocyanate, xylene, diisocyanate, triphenylmethane diisocyanate and tris(4-phenol isocyanate) thiophosphate and may be used as a suitable, adhesive polymer.

Polyols, which can be used in the polymerization, are, for example, oxirans such as ethylene oxide, propylene oxide, butylene oxide or also tetrahydrofuran or ethylene glycol, propylene glycol, trimethylol propane or glycerin.

Alternatively, the third layer of containers (A) and/or (B) may also comprise a layer of a synthetic polymer from the group comprising the polyesters, polyamides, polyethylene terephthalates, polybutylene terephthalates and the polyolefins other than polymer (I).

In a further particularly preferred embodiment, a product as contemplated herein is exemplified in that
the third layer of container (A) comprises a layer of a synthetic polymer selected from the group comprising polyurethanes, polyesters, polyamides, polyethylene terephthalates, polybutylene terephthalates and the polyolefins other than polymer (I) and/or
the third layer of container (B) comprises a layer of a synthetic polymer selected from the group comprising polyurethanes, polyesters, polyamides, polyethylene terephthalates, polybutylene terephthalates and the polyolefins other than polymer (I).

In a further particularly preferred embodiment, a product as contemplated herein is exemplified in that
the containers (A) and (B) have a third layer of a synthetic polymer (II), which is structurally different from the synthetic polymer (I), wherein,
the third layer of container (B) comprises a layer of a synthetic polymer selected from the group comprising polyurethanes, polyesters, polyamides, polyethylene terephthalates, polybutylene terephthalates and the polyolefins other than polymer (I).
the third layer of container (B) comprises a layer of a synthetic polymer selected from the group comprising polyurethanes, polyesters, polyamides, polyethylene terephthalates, polybutylene terephthalates and the polyolefins other than polymer (I).

With regard to all further details of the polymer layer thicknesses, layer sequences and layer materials of the containers (A) and (B), reference is made in full to EP 2 738 117 A1. The presence of additional layers of further polymers, which are between the pouch contents and the metallic metal layer, may slow down and/or possibly inhibit to some extent the diffusion of the hydrogen peroxide through these polymer layers and thus retard the reaction between hydrogen peroxide and the outer aluminum layer of the pouch . . . . At the same time, however, the manufacture of pouches, often coated with different materials, is a high cost factor, which can increase the price of the color changing products unduly. For economic reasons therefore, it is preferred if the pouches (A) and (B) as contemplated herein includes as few different layers as possible. Due to the use of the complexing agents as contemplated herein from the group (A2), the reaction between hydrogen peroxide and the aluminum foil of the pouch can now be suppressed or minimized, without coating the inside of the pouch with many further materials. A further particularly preferred embodiment is therefore exemplified in that the containers (A) and (B) includes not more than 7, preferably not more than 6, more preferably not more than 5, more preferably not more than 4 and quite particularly of not more than 3 different layers.

In a further particularly preferred embodiment, a product as contemplated herein is exemplified in that
the containers (A) includes not more than 7, preferably not more than 6, more preferably not more than 5, more preferably not more than 4 and quite particularly of not more than 3 different layers.
the containers (B) includes not more than 7, preferably not more than 6, more preferably not more than 5, more preferably not more than 4 and quite particularly of not more than 3 different layers.

For the purposes of the present disclosure, different layers are understood to be, layers of different materials, that is, polymers and metals.

In a particularly preferred embodiment, the product as contemplated herein is comprised of two pouch-shaped containers (A) and (B), which respectively contain the preparations (A) and (B) and which are together in an aerosol pressure can (C). In this embodiment, the aerosol pressure can has an outlet opening (D), which is connected to container (A) and container (B).

In a further particularly explicitly preferred embodiment, a product as contemplated herein is exemplified in that the first container (container A) and the second container (container B) together are in one aerosol pressure can (C), the aerosol pressure can (C) has an outlet opening (D), which is connected with container (A) and with container (B) and the space between the outer walls of the two containers (A) and (B) and the inner wall of the aerosol pressure can (C) is filled with at least one propellant. In this case, the compositions (A) and (B) are separately formulated in the containers (A) and (B), but can be brought into contact by way of the dispensing opening (D). As long as the dispensing opening (for example, the valve) is not actuated, preparations (A) and (B) are separate and contact between the two preparations is made only by operating the dispensing opening (D).

The containers (A) and (B) can be arranged next to, above or below one another within the aerosol pressure can (C). The capacity of the containers (A) and (B) may each be from about 10 cm$^3$ to about 1000 cm$^3$, and the capacity of the containers (A) and (B) may be the same or different. Preferably, the capacity of containers (A) and (B) is the same; The aerosol pressure can (C) has a dispensing opening (D), which is connected to the two containers (A) and (B). During the removal, the two preparations (A) and (B) are withdrawn simultaneously from the common outlet opening and mixed with one another only in or directly after the dispensing opening (D). Thus, preparations (A) and (B) come into contact with one another only during or directly after passage through the dispensing opening (D) and form the ready-for-use color-changing agent.

The dispensing opening (D) may, for example, be a valve, and the preparations (A) and (B) are removed over the common dispensing opening (D) by pressing the valve. In a further particularly preferred embodiment, a product as contemplated herein is exemplified in that the first container (container A) and the second container (container B) together are in the interior of one aerosol pressure can (C), the aerosol pressure can (C) has an dispensing opening (D), which is connected with container (A) and with container (B) and the space between the outer walls of the two containers (A) and (B) and the inner wall of the aerosol pressure can (C) is filled with at least one propellant gas from the group comprising propane, propene, n-butane, isobutane, isobutene, pentane, isopentane, isopentane, air, nitrogen, argon, $N_2O_3$ and/or $CO_2$.

In the aforementioned, preferred embodiment, the product as contemplated herein comprises an outer compressed gas container. Vessels of metal (aluminum, tin plate, tin), of protected or non-splintering plastic or glass, which is coated with plastic on the outside, are suitable as compressed gas containers, in the choice of which, compressive and breaking strength, corrosion resistance, ease of filling as well as aesthetic aspects, handiness, printability, etc. play a role. Particularly preferred compressed gas containers are vessels made of metal (aluminum, tinplate, tin).

As described above, the two separate containers (A) and (B) particularly preferably are two deformable pouches, preferably of aluminum, laminated with a synthetic polymer (I), each of which is connected to the dispensing opening (D). The dispensing opening (D) is a pressure-vessel dispensing device. Both pouches are housed in a can-shaped pressure vessel, the pressure vessel, together with the pressure-vessel dispensing device, sealing the product externally with a pressure-tight seal. The space between the outer wall of the pouches and the inner wall of the pressure container is filled with at least one propellant gas. Corresponding dispensers are also known, for example, from US 2009/0108021 A1.

Particularly good effects as contemplated herein are achieved when the internal pressure of the pressure vessel is at least about 1.8 bar, in particular at least about 2.5 bar.

The product furthermore comprises a dispensing device (corresponding to the dispensing opening D), which may have a valve for dispensing the application mixture. In a preferred embodiment as contemplated herein, the valve has a valve disc, which is coated with a varnish or a polymeric plastic, and an equally flexible element with restoring characteristics, which restores the valve to the closing position (=rest position of the valve) after the actuation is completed. Corresponding cosmetic products, in which the aerosol dispensing device comprises a valve, which has a valve cone and/or a flexible element with return characteristics, which is coated with a varnish or a polymeric plastic, are also preferred as contemplated herein.

In a further preferred embodiment as contemplated herein, the flexible element can be designed with return characteristics as a spiral spring or a compression spring. In a further preferred embodiment as contemplated herein, the flexible element of the valve with restoring characteristics can be designed in one piece with the valve cone and have flexible legs. This spring may be a metal or plastic spring.

All valves used as contemplated herein preferably have an internally coated valve disc, the coating and valve material being compatible with one another. If aluminum valves are used as contemplated herein, the valve discs thereof may be coated internally, for example, with a Microflex coating. If tinplate valves are used as contemplated herein, the valve actuators can be coated internally, for example, with PET (polyethylene terephthalate). The containers used, which may be made of, for example, of tinplate or aluminum, aluminum containers being preferred as contemplated herein, must also be lacquered or coated on the inside in view of the corrosiveness of the water in oil emulsions used as contemplated herein.

If the product as contemplated herein is applied using a pressure can, the dispensers contain at least one propellant gas from the group comprising propane, propene, n-butane, iso-butane, iso-butene, n-pentane, pentene, iso-pentane, iso-pentene, air, nitrogen, argon, $N_2O$, and/or $CO_2$ Within this group, the permanent gases such as air, nitrogen, argon, $N_2O$ and/or $CO_2$ are preferred, nitrogen, argon and/or $CO_2$ being particularly preferred.

Furthermore, it has proven to be preferable if the propellant gases are also contained in the aerosol pressure cans (C) at certain pressures. In a preferred embodiment, the aerosol pressure can (C) as contemplated herein contains one or more propellants at a pressure of from about 3-12 bar, preferably of from about 4 to about 10 bar and particularly of from about 5 to about 8 bar, based on the pressure of the propellant gases between the pouch-shaped chambers (A) and (B) and the pressure can.

Preferably, the individual product compositions are mixed in the course of the product application into an overall formulation in order to exhaust the complete effectiveness of the overall formulation as well as to facilitate the product application in general. For this purpose, the dispenser expediently comprises, in addition to the containers (A), (B), an output head, within which the preparations (A) and (B) are conveyed from the chambers to the dispensing opening (D). Moreover, a suitable mixing device is provided in the dispensing head, which ensures the desired mixing of preparations (A) and (B) upstream from the dispensing opening (D) before the mixed overall formulation, that is, (A)+(B) is delivered through the dispensing opening (D). For example, a generic dispenser with a comparable mixing device is known from DE 3729491 A1, but the mixing device there has only a very short mixing distance. As contemplated herein, such a mixing device is integrated structurally directly into the dispensing head or alternatively arranged as a separate component within the dispensing head. Within the meaning as contemplated herein, static mixers or comparably-acting mixing sections for example, through which the ready-to-use preparations (A) and (B) flow and are mixed sufficiently, are suitable mixing devices. For this purpose, such a mixing section has, as a rule, suitable flow inserts or flow distorters, which, due to turbulences produced by flow dynamics, bring about mixing of the individual fluid components One of the decisive factors deciding the quality of mixing of the individual fluid components, here the preparations (A) and (B), within the mixing device is the effect of the targeted matching of the length of the mixing distance as well as the design of the flow inserts on the rheological properties of preparations (A) and (B). Usually, defined minimum lengths of the mixing distance are required for adequate mixing results of the mixing device as contemplated herein. For this reason, the mixing distance of the mixing device as contemplated herein preferably is designed so that a defined minimum length of the mixing distance is guaranteed without giving up a compact overall construction of the mixing device and, with that, of the dispensing head. In this way, adequate mixing results are guaranteed and, at the same time, the desired compact external dimensions of the mixing device and of the dispensing head are ensured. For this purpose, the mixing distance is designed, for example, spirally or comparatively compact within the dispensing head.

The volume selected for the individual containers (A) and (B) depends on the desired ratio of the volumes of preparations (A) and (B). Preferably, the capacities of the chambers (A) and (B are the same.

As contemplated herein, the quantitative ratio of preparation (A) to preparation (B) ranges from about 1:3 to about 3:1, preferably from about 1:1.5 to about 1.5:1 and particularly is 1:1.

The products as contemplated herein may be used in methods for the oxidative changing of the hair color. These processes are distinguished by a particular ease of application, since the costly and error-prone production of the use mixtures by the consumer is dispensed with. What has been said concerning the product as contemplated herein applies mutatis mutandis to further preferred embodiments of the method as contemplated herein.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A product for oxidatively changing the color of keratinic fibers, comprising at least two preparations (A) and (B), which are produced separately from one another, wherein
the first preparation (A) comprises, in a cosmetic carrier,
(A1) hydrogen peroxide and
(A2) at least one chelating agent chosen from the group comprising 1-hydroxyethane-1,1-diphosphonic acid (HEDP), ethylenediaminetetramethylenephosphonic acid (EDTMP), diethylenetriaminepentamethylenphosphonic acid (DTPMP), aminotrimethylenephosphonic acid (ATMP), N,N-bis[2-[bis(carboxymethyl)amino] ethyl]glycine, ethylene-diamine-N,N'-disuccinic acid (EDDS), 2-hydroxypropylenediamine-N,N'-disuccinic acid (HPDDS), ethylenediamine-N,N'-diglutaric acid (EDDG), ethylenediamine-N,N'-bis-(orthohydroxyphenyl)acetic acid (EDDHA),
the second preparation (B), in a cosmetic carrier, comprises
(B1) at least one alkalizing agent,
the preparation (A) is produced in a first container (container A), which comprises at least two layers, wherein
an inner layer of the container A comprises a layer of a synthetic polymer (I) and
an outer layer of the container A comprises a metal layer,
preparation (B) is produced in a second container (container B), which comprises at least two layers, wherein
an inner layer of the container B comprises a layer of a synthetic polymer (I) and
an outer layer of the container B comprises a metal layer, wherein
the first container (container A) is a pouch with a total layer thickness of from about 2 to about 400 μm (micrometers), and/or
the second container (container B) is a pouch with a total layer thickness of from about 2 to about 400 μm (micrometers).

2. The product of claim 1, wherein the first preparation (A), based on the total weight of preparation (A), comprises the (A1) hydrogen peroxide in an amount of from about 0.5 to about 20.0% by weight.

3. The product of claim 1, wherein the first preparation (A) comprises the one or more chelating agents (A2) in a total amount of from about 0.01 to about 5.5% by weight, based on the total weight of preparation (A).

4. The method of claim 1, wherein the first preparation (A) comprises—
as (A2), at least one chelating agent chosen from the group comprising 1-hydroxyethane-1,1-diphosphonic acid (HEDP), ethylenediaminetetramethylenephosphonic acid (EDTMP), diethylene-triaminepentamethylenephosphonic acid (DTPMP), aminotrimethylene phosphonic acid (ATMP), and/or a physiologically tolerated salt hereof.

5. The product of claim 1, wherein the first preparation (A) comprises—
as (A2), 1-hydroxyethane-1,1-diphosphonic acid (HEDP) and/or a physiologically tolerated salt hereof as chelating agent.

6. The product of claim 1, wherein the ratio by weight of the total amount of the hydrogen peroxide (A1), included in the preparation (A) to the total amount of the chelating agents from group (A2), included in the preparation (A) is from about 1.0 to about 30.0.

7. The product of claim 1, wherein the first preparation (A), based on the total weight of preparation (A), additionally comprises
(A3) 2,6-dipicolinic acid, benzoic acid and/or salicylic acid and/or their physiologically tolerated salts in a total amount of from about 0.05 to about 1.5% by weight.

8. The product of claim 1, wherein
the first preparation (A) is an aqueous preparation with a pH of from about 1.5 to about 5.0 and
the second preparation (B) is an aqueous preparation with a pH of from about 7.5 to about 12.5.

9. The product of claim 1, wherein
the outer layer of container (A) comprises a layer of aluminum with a thickness of from about 5 to about 50 μm (micrometers), and/or
the outer layer of container B comprises an aluminum layer with a thickness of from about 5 to about 50 μm (micrometers).

10. The product of claim 1, wherein
the containers (A) and (B) have a third layer of a synthetic polymer (II), which is structurally different from the synthetic polymer (I).

11. The product of claim 10, wherein
the third layer of container (A) comprises a layer of a synthetic polymer selected from the group comprising polyurethanes, polyesters, polyamides, polyethylene terephthalates, polybutylene terephthalates and the polyolefins other than polymer (I) and/or
the third layer of container (B) comprises a layer of a synthetic polymer selected from the group comprising polyurethanes, polyesters, polyamides, polyethylene terephthalates, polybutylene terephthalates and the polyolefins other than polymer (I).

12. The product of claim 1, wherein
the first container (container A) and the second container (container B) together are in an interior of one aerosol pressure can (C),
the aerosol pressure can (C) has a dispensing opening (D), which is connected with container (A) and with container (B) and
the space between the outer walls of the two containers (A) and (B) and the inner wall of the aerosol pressure can (C) is filled with at least one propellant.

13. The product of claim 1, wherein the first preparation (A), based on the total weight of preparation (A), comprises
the (A1) hydrogen peroxide in an amount of from about 2.5 to about 12.0% by weight,
the (A2) one or more chelating agents in a total amount of from about 0.7 to about 2.5% by weight, and
wherein the ratio by weight of the total amount of the hydrogen peroxide (A1), included in the preparation (A) to the total amount of the chelating agents from group (A2), included in the preparation (A) is from about 3.3 to about 13.5.

14. The product of claim 1, wherein
the first preparation (A) is an aqueous preparation with a pH of from about 2.6 to about 3.5 and
the second preparation (B) is an aqueous preparation with a pH of from about 8.9 to about 10.5.

15. The product of claim 1, wherein
the pouch of the first container (container A) with has a total layer thickness of from about 50 to about 200 μm (micrometers), and/or
the pouch of the second container (container B) has a total layer thickness of from about 50 to about 200 μm (micrometers).

16. The product of claim 1, wherein
the inner layer of the container A comprises a layer of a synthetic polymer (I) chosen from the group of polyethylene, polypropylene, a polyethylene/polypropylene copolymer, poly-1-butene, a polyethylene/poly-1-butene copolymer, a polypropylene/poly-1-butene copolymer/and/or a polyethylene/poly-propylene/poly-1-butene copolymer, and/or
the inner layer of the container B comprises a layer of a synthetic polymer (I) chosen from the group of polyethylene, polypropylene, a polyethylene/polypropylene copolymer, poly-1-butene, a polyethylene/poly-1-butene copolymer, a polypropylene/poly-1-butene copolymer/and/or a polyethylene/poly-propylene/poly-1-butene copolymer.

17. A product for oxidatively changing the color of keratinic fibers, comprising at least two preparations (A) and (B), which are produced separately from one another, wherein
the first preparation (A) comprises, in a cosmetic carrier,
(A1) hydrogen peroxide and
(A2) at least one chelating agent chosen from the group comprising 1-hydroxyethane-1,1-diphosphonic acid (HEDP), ethylenediaminetetramethylenephosphonic acid (EDTMP), diethylenetriaminepentamethylenphosphonic acid (DTPMP), aminotrimethylenephosphonic acid (ATMP), N,N-bis[2-[bis(carboxymethyl)amino] ethyl]glycine, ethylene-diamine-N,N'-disuccinic acid (EDDS), 2-hydroxypropylenediamine-N,N'-disuccinic acid (HPDDS), ethylenediamine-N,N'-diglutaric acid (EDDG), ethylenediamine-N,N'-bis-(orthohydroxyphenyl)acetic acid (EDDHA),
the second preparation (B), in a cosmetic carrier, comprises
(B1) at least one alkalizing agent,
the preparation (A) is produced in a first container (container A), which comprises at least two layers, wherein
an inner layer of the container A comprises a layer of a synthetic polymer (I) and
an outer layer of the container A comprises a metal layer,
preparation (B) is produced in a second container (container B), which comprises at least two layers, wherein
an inner layer of the container B comprises a layer of a synthetic polymer (I) and
an outer layer of the container B comprises a metal layer, wherein
the inner layer of the container A comprises a layer of a synthetic polymer (I) chosen from the group of polyolefins, and/or
the inner layer of the container B comprises a layer of a synthetic polymer (I) chosen from the group of polyolefins.

18. A product for oxidatively changing the color of keratinic fibers, comprising at least two preparations (A) and (B), which are produced separately from one another, wherein
the first preparation (A) comprises, in a cosmetic carrier,
(A1) hydrogen peroxide and
(A2) at least one chelating agent chosen from the group comprising 1-hydroxyethane-1,1-diphosphonic acid (HEDP), ethylenediaminetetramethylenephosphonic acid (EDTMP), diethylenetriaminepentamethylenphosphonic acid (DTPMP), aminotrimethylenephosphonic acid (ATMP), N,N-bis[2-[bis(carboxymethyl)amino]ethyl]glycine, ethylene-diamine-N,N'-disuccinic acid (EDDS), 2-hydroxypropylenediamine-N,N'-disuccinic acid (HPDDS), ethylenediamine-N,N'-diglutaric acid (EDDG), ethylenediamine-N,N'-bis-(orthohydroxyphenyl)acetic acid (EDDHA),
the second preparation (B), in a cosmetic carrier, comprises
(B1) at least one alkalizing agent,
the preparation (A) is produced in a first container (container A), which comprises at least two layers, wherein
an inner layer of the container A comprises a layer of a synthetic polymer (I) and
an outer layer of the container A comprises a metal layer,
preparation (B) is produced in a second container (container B), which comprises at least two layers, wherein
an inner layer of the container B comprises a layer of a synthetic polymer (I) and
an outer layer of the container B comprises a metal layer, wherein
the inner layer of the container (A) comprises a synthetic polymer (I) with a thickness of from about 20 to about 200 μm (micrometers), and/or
the inner layer of the container B comprises a layer of a synthetic polymer (I) with a thickness of from about 20 to about 200 μm (micrometers).

19. A product for oxidatively changing the color of keratinic fibers, comprising at least two preparations (A) and (B), which are produced separately from one another, wherein
the first preparation (A) comprises, in a cosmetic carrier,
(A1) hydrogen peroxide and
(A2) at least one chelating agent chosen from the group comprising 1-hydroxyethane-1,1-diphosphonic acid (HEDP), ethylenediaminetetramethylenephosphonic acid (EDTMP), diethylenetriaminepentamethylenphosphonic acid (DTPMP), aminotrimethylenephosphonic acid (ATMP), N,N-bis[2-[bis(carboxymethyl)amino]ethyl]glycine, ethylene-diamine-N,N'-disuccinic acid (EDDS), 2-hydroxypropylenediamine-N,N'-disuccinic acid (HPDDS), ethylenediamine-N,N'-diglutaric acid (EDDG), ethylenediamine-N,N'-bis-(orthohydroxyphenyl)acetic acid (EDDHA),
the second preparation (B), in a cosmetic carrier, comprises
(B1) at least one alkalizing agent,
the preparation (A) is produced in a first container (container A), which comprises at least two layers, wherein
an inner layer of the container A comprises a layer of a synthetic polymer (I) and
an outer layer of the container A comprises a metal layer,
preparation (B) is produced in a second container (container B), which comprises at least two layers, wherein
an inner layer of the container B comprises a layer of a synthetic polymer (I) and
an outer layer of the container B comprises a metal layer, wherein
the container (A) comprises not more than 7 different layers, and/or
the container (B) comprises not more than 7 different layers.

* * * * *